United States Patent [19]
Shinjou et al.

[11] Patent Number: 5,211,661
[45] Date of Patent: May 18, 1993

[54] ARTIFICIAL LIVING BODY COMPOSITE MATERIAL

[75] Inventors: Kiyoshi Shinjou, Nagoya; Shigehide Takagi, Narashino, both of Japan

[73] Assignee: Sumitomo Cement Co., Ltd., Tokyo, Japan

[21] Appl. No.: 570,997

[22] Filed: Aug. 22, 1990

Related U.S. Application Data

[60] Continuation of Ser. No. 506,482, Apr. 6, 1990, abandoned, which is a division of Ser. No. 150,418, filed as PCT/JP87/00304, May 15, 1987, published as WO 87/06843, Nov. 19, 1987, abandoned.

[30] Foreign Application Priority Data

May 16, 1986 [JP] Japan .................................. 61-109466

[51] Int. Cl.⁵ .............................................. A61F 2/28
[52] U.S. Cl. ........................................ 623/16; 623/66
[58] Field of Search ................... 623/16, 11, 12, 18, 623/66

[56] References Cited

U.S. PATENT DOCUMENTS

| | | | |
|---|---|---|---|
| 4,237,559 | 12/1980 | Borom | 623/16 |
| 4,430,760 | 2/1984 | Smestad | 623/10 |
| 4,576,608 | 3/1986 | Homsy | 623/11 |
| 4,626,392 | 12/1986 | Kondo et al. | 501/1 X |
| 4,657,548 | 4/1987 | Nichols | 604/93 X |

FOREIGN PATENT DOCUMENTS

0169001 1/1986 European Pat. Off. ............. 623/16

OTHER PUBLICATIONS

"Resorbierbare Calciumphosphatkeramik im Tierexperiment unter Belastung" Langenbecks Arch. Chir., 343, pp. 173-181 (1977).

"Experimenteller Knochenersatz durch resorbierbare Calciumphosphat-Keramik" Langenbecks Arch. Chir., 341, pp. 77-86 (1976).

"Biodegradable ceramic implants in bone" Oral sarg., 32, pp. 336-346 (1971).

*Primary Examiner*—David Isabella
*Attorney, Agent, or Firm*—Armstrong, Westerman, Hattori, McLeland & Naughton

[57] ABSTRACT

An artificial living body composite material comprising an artificial bone portion formed to a desired shape and size, and an inclusion membrane comprising an organic polymer material as a main constituent; optionally the artificial bone portion being composed of a base member and a coating layer.

7 Claims, 4 Drawing Sheets

ARTIFICIAL LIVING BODY COMPOSITE MATERIAL

This application is a continuation of application Ser. No. 506,482, filed Apr. 6, 1990, now abandoned, which is a continuation of Ser. No. 150,418, filed as PCT/JP87/00304, May 15, 1987, published as WO 87/06843, Nov. 19, 1987, now abandoned.

DESCRIPTION

1. Technical Field

The present invention relates to an artificial living body material. More particularly, the present invention relates to an artificial living body hard tissue material, especially an artificial bone material, for substitution or filling.

2. Background Art

In a human body or other animal body, if a bone is damaged by disease or an external wound or if a bone is excised by a surgical operation because of a malignant tumor, the damaged bone portion or bone-excised portion has generally been replaced or filled with a bone of the living body per se extracted from another part of the living body. Recently, an artificial living body hard tissue material (hereinafter referred to as "artificial bone") has been used for the replacement or filling of such a damaged bone portion or bone-excised portion.

In practice, however, the replacement or filling with an artificial bone involves several problems.

For example, during an excising of a malignant tumor at the sternum, a part of the sternum is replaced with an artificial bone by a surgical operation. However, a maintenance of the function of the sternocalvicular joint is not taken into consideration and proper measures have not been taken accordingly. Therefore, after the operation, problems such as a dislocation or deviation of the sternocalvicular joint, a formation of carbuncle holes, a feeling of pain, and a degradation of the appearance arise.

Furthermore, in the case of a malignant tumor in the vicinity of the knee, in order to preserve the patient's lower limb, an artificial joint is often inserted after excision of the tumor. However, the surrounding soft tissue is also excised and the problem of a weak joint arises, and therefore, a hinge type artificial knee joint has been used. In this case, even if a weak joint is prevented, the motion of the artificial joint is very different from the motion of the knee joint, and a breakage or slackening of the artificial joint or a complication such as formation of carbuncle holes occurs. Moreover, since a large piece of the normal bone also must be excised, the invasion by the operation is great. Therefore, at the present, a multicenter artificial joint is used instead of the above-mentioned artificial joint, but since the surrounding soft tissue is excised, a weak joint is readily caused, and since the function is bad, this artificial joint is inconvenient when used.

Moreover, where a bone tumor portion is excised and an artificial bone is suture-secured to a natural bone, a muscle, a ligament or other tissue of the living body with a metal wire, a silk thread or other suturing material, the artificial bone is readily broken or the secured artificial bone is easily dislocated.

DISCLOSURE OF THE INVENTION

It is a primary object of the present invention to provide an artificial living body material (artificial bone) which is characterized in that, when a bone in the living body is substituted or filled for an artificial living body hard tissue material, only the affected part, the focus part or the damaged part is excised, and the artificial bone is inserted into this part and fixed tightly, strongly and stably thereat, and thus dislocation or deviation does not occur in a joint or the like, the formation of carbuncle holes is prevented, no pain is felt, no aesthetic defects appear, the artificial bone is easily anchored strongly to a muscle or tendon, the function of a joint is preserved as much as possible, the artificial bone can be used stably for a long time, and external deviation of a worn piece does not occur.

In accordance with the present invention, there is provided an artificial living body composite material comprising an artificial living body hard tissue material portion (artificial bone portion) formed to have a desired shape and size and an inclusion membrane which includes therein the artificial bone portion, and is composed of an organic polymeric material as the main constituent.

Note, in the present invention, the term artificial bone includes an artificial joint.

Also, in the material of the present invention, the artificial bone may be composed of a base member and a coating layer.

BEST MODE FOR CARRYING OUT THE INVENTION

Figure 1A:
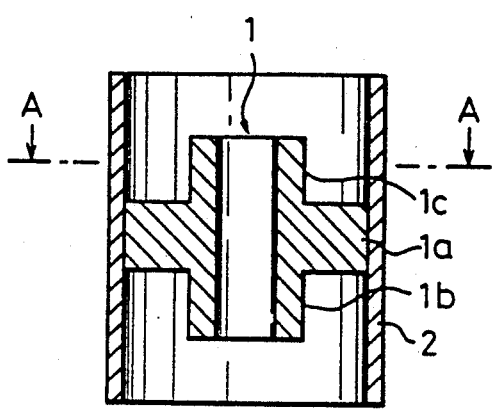
FIG. 1A is a diagram showing the longitudinal cross-section of one embodiment of the artificial living body composite material of the present invention.
Figure 1B:
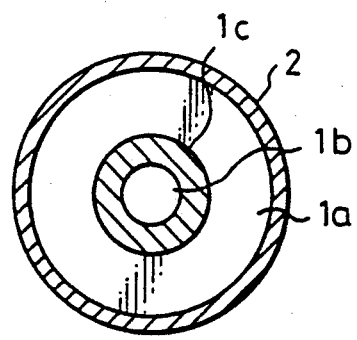
FIG. 1B is a diagram showing the lateral cross-section taken along the line A—A in the composite material shown in FIG. 1A.

An example of the artificial living body composite material of the present invention is illustrated in FIGS. 1A and 1B.

The artificial living body composite material shown in FIGS. 1A and 1B is used for substitution of a part of a thighbone and comprises an artificial bone portion 1 and an inclusion membrane 2. The artificial bone portion 1 comprises a hollow disk-shaped core 1a and a hollow projection 1c extending above and below the core 1a while surrounding a hollow part 1b of the core 1a. This artificial bone portion 1 is included within the inclusion membrane 2.

Figure 2A:
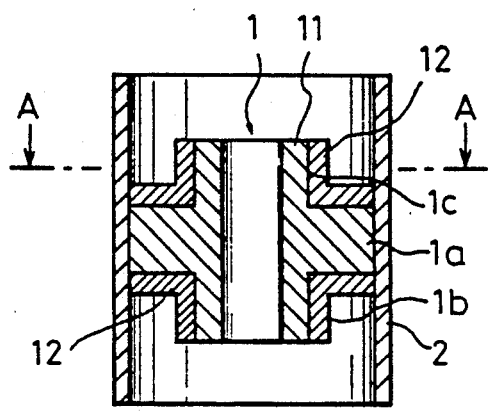
FIG. 2A is a diagram illustrating the longitudinal cross-section of another embodiment of the artificial living body composite material of the present invention.
Figure 2B:
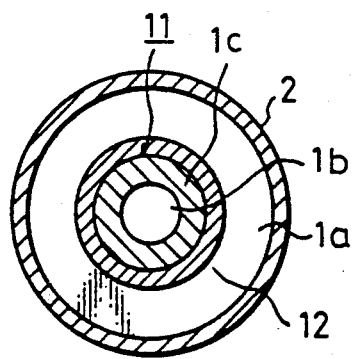
FIG. 2B is a diagram showing the lateral cross-section taken along the line A—A in the composite material shown in FIG. 2A.

Another example of the artificial living body composite material of the present invention is illustrated in FIGS. 2A and 2B.

The artificial living body composite material as shown in FIGS. 2A and 2B is also used for substitution of a part of a thighbone and comprises an artificial bone portion 1 and an inclusion membrane 2. The artificial bone portion 1 is composed of a base member 11 and a coating layer 12. The base material 11 comprises a hollow disk-shaped core 1a and a hollow projection 1c extending above and below the core 1a while surrounding a hollow part 1b of the core 1a.

The coating layer 12 is formed so as to coat the side faces of the core 1a and the hollow projection 1c of the base member 11. This artificial bone portion 1 having the above-mentioned double layer structure is included within a tube-shaped inclusion membrane 2.

Those artificial living body composite materials as shown in FIGS. 1A to 2B are inserted in an excised or faulty portion of a trunk (diaphysis) of a thighbone, the hollow projection 1c, which may have or may not have a coating layer, of the artificial bone portion is inserted in the medullary cavity to fix the artificial bone portion, and the inclusion membrane is sutured to the diaphysis portion so that the part extending from the core 1a, which may have or may not have a coating layer, of the artificial bone portion surrounds the outer side of the diaphysis portion and the inclusion membrane is also sutured tightly to the neighbouring muscle.

Figure 3:
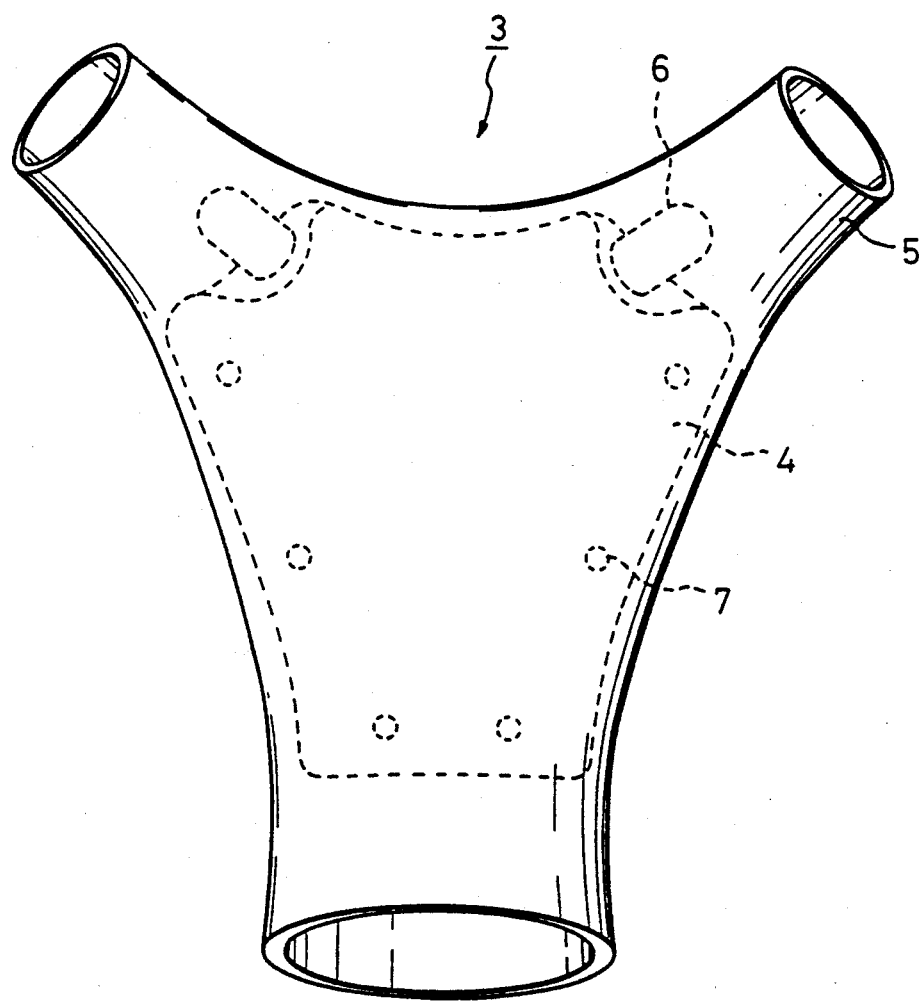
FIG. 3 is a diagram showing still another embodiment of the artificial living body composite material of the present invention.

Another example of the artificial living body composite material is shown in FIG. 3.

The artificial living body composite material 3 shown in FIG. 3 comprises an artificial sternum material 4 and an inclusion membrane 5 covering the sternum material 4 and being composed of a fabric of a synthetic fiber (for example, a polyester fiber) or a porous tetrafluoethylene sheet.

Further, the artificial living body composite material may have a base member consisting of the artificial bone material 4 as shown in FIG. 3 and a coating layer formed on the surface of the base member.

The artificial living body composite material of the present invention is firmly sutured and fixed through the inclusion membrane thereof to not only the bone portion but also the neighbouring muscle or tendon and other soft tissue (peritoneum, joint capsule, periosteum or the like).

In the artificial living body composite material of the present invention, the artificial bone portion or base member thereof is formed from at least one member selected from ceramics, carbon, metals (including alloys), and rigid organic synthetic resin as the main constituent, to a desired shape and size. As the artificial bone portion-forming ceramics or its base member-forming ceramics there can be used, for example, at least one member selected from alumine ($Al_2O_3$), zirconia ($ZrO_2$) and calcium phosphate. As the artificial bone-forming or its base member-forming metal, there can be mentioned at least one member selected from stainless steel, titanium, tantalum, titanium alloys, nickel-chromium alloys, nickel-chromium-cobalt alloys and cobalt-chromium-molybdenum alloys.

As the artificial bone portion or its base member-forming rigid organic material, there can be used at least one member selected from high-density polyethylene resins, polytetrafluoroethylene resins, polymethyl methacrylate resins, polyester resins and silicone resins.

The artificial bone portion or its base member-forming material may be a porous material or a non-porous material. For example, a porous sintered body of calcium phosphate is used as the artificial bone portion-forming material in the artificial living body composite material of the present invention.

In the synthetic calcium phosphate used for this purpose, the calcium/phosphorus molar ratio is in the range of from 1.30 to 1.80. Calcium phosphate [$Ca_3(PO_4)_2$] and hydroxyapatite [$Ca_{10}(PO_4)_6(OH)_2$] in which the calcium/phosphorus molar ratio is in the range of from 1.60 to 1.70 are preferred, and calcium phosphate which is synthesized by the sol-gel method and freeze-dried is especially preferred.

The sintered body of calcium phosphate can be prepared, for example, in the following manner.

More specifically, calcium phosphate (100 parts by weight) is homogeneously mixed with organic synthetic resin particles (0 to 70 parts by weight) of a truly spherical shape having a particle size of 1 to 600 micron and an organic polymer fiber (1 to 5 parts by weight) having a diameter of 1 to 30 microns, the mixture is formed into a molded body having a desired shape and size and the molded body is heated at a temperature of 200° to 800° C. to thermally decompose and remove the organic resin particles and organic polymer fiber, whereby a porous molded body is obtained. The porous molded body is then sintered at a temperature or 800° to 1350° C., preferably 1000° to 1350° C., and the obtained porous sintered body is cut to a desired shape and size.

As the pore-forming organic synthetic resin particles, there can be used particles of a polypropylene resin, a polymethyl methacrylate resin or a polystyrene resin. As the organic polymer fiber, there can be used an animal hair, a silk fiber, a cellulose fiber, a polyester fiber or a polyolefin fiber.

The so-prepared porous calcium phosphate sintered body has a great number of truly spherical independent pores having a size of 1 to 600 microns and a great number of capillary void paths having a void diameter of 1 to 30 microns. The truly spherical independent pores communicate with one another and the exterior space through the capillary void paths. The pores have a truly spherical shape or a substantially truly spherical shape, and preferably the pores are uniformly distributed in the sintered body. These pores provide spaces recognized as bone-repairing and activating sites by octeocytes, that is, cell recognition sites (cell residence spaces) for the repair of the bone. Octeocytes like to stay in truly spherical spaces having a specific curvature, and preferably the pore diameter is 1 to 600 microns, especially 10 to 300 microns. If the pores have a spherical shape or a substantially spherical shape, the mechanical strength of the obtained porous body is increased. The capillary void paths allow a selective intrusion of osteoclasts, osteoblasts, body fluids and leucocytes but does not allow an intrusion of collagen fibers and macrophages having a large diameter to prevent an abnormal propagation of collage fibers, formation of inflammatory false joints, and a generation of cancer. The above-mentioned cells, which have intruded into the pores, like to stay in the pores having the above-mentioned shape and size, and control the speed of regeneration of the bone and re-absorption of the bone and promote the generation of a reborn bone.

Where the artificial living body composite material of the present invention comprises an artificial bone portion composed of a base member and a coating layer, and an inclusion membrane, this type of artificial living body composite material includes the various embodiments as indicated, for example, in Table 1.

However, the artificial living body composite material of the present invention is not limited to those embodiments.

TABLE 1

| Embodi-ment | Artificial bone portion | | Inclusion membrane |
|---|---|---|---|
| | Base member | Coating layer | |
| 1 | Hydroxyapatite (HAP) | Porous or non-porous hydroxyapatite (HAP) | Polytetrafluoroethylene (PTFE) porous membrane |
| 2 | Caramics (alumina or zirconia | Porous or non-porous hydroxyapatite (HAP) | Polytetrafluoroethylene (PTFE) porous membrane |
| 3 | Ceramics (alumina or zirconia) | Porous or non-porous ceramics (alumina or zirconia, HAP, etc. | Polytetrafluoroethylene (PTFE) porous membrane |
| 4 | Metals (which may be shaped memory alloys) | Porous or non-porous HAP, alumina, zirconia, etc. | Polytetrafluoroethylene (PTFE) porous membrane |
| 5 | Metal (which may be shaped memory alloys) | Porous or non-porous metals | Polytetrafluoroethylene (PTFE) porous membrane |
| 6 | Carbon material (which may be shaped carbon fiber materials) | Porous or non-porous metals | Polytetrafluoroethylene (PTFE) porous membrane |
| 7 | Carbon material (which may be shaped carbon fiber materials) | Porous or non-porous ceramics (alumina, zirconia, HAP, etc. | Polytetrafluoroethylene (PTFE) porous membrane |
| 8 | Carbon material (which may be shaped carbon fiber materials) | Double layer of porous or non-porous ceramics and metal layers | Polytetrafluoroethylene (PTFE) porous membrane |

In the composite material of the present invention, the inclusion membrane including the artificial bone portion therein is very effective for fixing the composite material stably in the living body. By the term "including" is meant the state where the majority of the artificial bone portion is included within the space defined by the inclusion membrane, and a part of the artificial bone portion, for example, a portion of the coating layer, may be exposed to the external space or a part of the inner face of the inclusion membrane may be slightly separated from a part of the outer surface of the artificial bone portion. The inclusion membrane may be in the form of any of a sheet, a tube and a bag.

The main constituent of the inclusion membrane may be formed of a fiber composed of an organic polymeric material, and may have a shape of a sheet such as a woven fabric, a knitted fabric, a felt, a net or a non-woven fabric, or may be a film composed of an organic polymeric material. As the organic polymeric material, there are generally used polyester resins such as a polyethylene terephthalate resin and fluorine-containing organic materials such as a polytetrafluoroethylene resin. The polytetrafluoroethylene film may be a sheet rendered porous by drawing and expansion.

Preferably, the main constituent of the inclusion membrane is stretchable and shrinkable in both the longitudinal and lateral directions, and the texture and structure of the main constituent and the treatment conditions such as the drawing conditions are selected according to the desired stretching or shrinking degree. For example, there can be mentioned a case where the same stretchability or shrinkability is required in both the longitudinal and lateral directions, or a case where the stretchability or shrinkability in one direction should be larger than the stretchability or shrinkability in the other reaction. More specifically, there can be mentioned a case where the elongation in the longitudinal direction is lower than in the lateral direction and the shrinkage in the longitudinal direction is higher than in the lateral direction, or a case where the elongation in the longitudinal direction is lower and the shrinkage in the longitudinal direction is higher.

As the membrane as the main constituent of the inclusion membrane, there can be used, for example, a polytetrafluoroethylene sheet, a porous polytetrafluoroethylene sheet, a polyester sheet, a polyester fiber fabric, a net, and a non-woven fabric. Where a knitted or woven fabric, especially one having a shape of a tube, is used as the inclusion membrane, preferably the woven or knitted fabric has a structure such that the elongation in the longitudinal direction is low and the shrinkage or compactness in the longitudinal direction is high. The inclusion membrane is effective for forming an artificial ligament, artificial joint capsule, artificial fascia or artificial periosteum covering the artificial bone portion, and is especially preferable for an artificial load joint.

The inclusion membrane used in the present invention is sutured to a bone muscle, a tendon, a ligament or other tissue in the state where the inclusion membrane is wound around the artificial bone portion (inclusive of the artificial joint portion) or the artificial bone portion is included within the artificial bone portion, whereby the artificial bone portion is easily fixed at a predetermined position and the load on the artificial portion is moderated or dispersed, or breaking or destruction of the bone of the living body by the load is prevented. Even if the living material is broken, a worn piece is prevented from separating from the living body. By dint of these effects of the inclusion membrane, the artificial living body composite material of the present invention can be applied even to a load joint. The artificial bone portion used in the present invention may contain at least one member selected from bone-derived proteins and collagen derivatives in the state where the main constituent of the artificial bone portion is impregnated or covered with this member. In this case, preferably the main constituent of the artificial bone portion is composed of a porous body such as a porous calcium phosphate sintered body, which is impregnated with the above-mentioned member. The bone-derived protein or collagen derivative thus contained in the artificial bone portion promotes the formation and generation of a reborn bone or collagen.

The inclusion membrane used in the present invention may contain at least one member selected from bone-derived proteins and collagen derivatives in the state where the main constituent is impregnated or covered with this member. The bone-derived protein or collagen derivative thus contained in the inclusion membrane promotes the generation and formation of a reborn bone.

A polytetrafluoroethylene (PTFE) resin material is valuable for use as the fluorine-containing organic polymeric material constituting the inclusion membrane of the present invention, and a porous PTFE material formed by extrusion-molding a PTFE powder together with a lubricant, which has fine fibers, knots gathering these fibers and fine pores formed among the fibers, is especially preferred. This porous PTFE material is marketed under the tradename of "Goretex". In this porous PTFE material (sheet), the soft tissue of the living body intrudes into fine pores or net meshes and comes into direct contact with the artificial bone portion composed of, for example, the porous calcium phosphate sintered body or with the coating layer thereof. Since this artificial bone portion or the coating layer consisting of the above-mentioned material has a very good affinity with the living body, a very high living tissue-receiving effect is attained, and cartilage cells intrude into the surface of the artificial bone portion or coating layer thereof consisting of the porous calcium phosphate sintered body to form a cartilage at these parts. Accordingly, the artificial living body composite material can be stably fixed to the living body.

Even in the case where the artificial bone portion is composed of a base member and a coating layer, since the base member consists of a high strength metal (or alloy), sintered ceramics (alumina, zirconia, HAP, etc.), the artificial bone portion has a satisfactorily high strength. Also, the coating layer in the artificial bone portion can receive the intrusion of the living tissue and cause a bone structure to be formed.

The above-mentioned effects of the present invention are especially prominent when the inclusion membrane is composed of a fluorine-containing organic polymeric material or a polyester material, particularly a porous PTFE material (Goretex), and can make the fixation of the artificial living body composite material to the living body stable and can improve the motility of the fixed portion.

According to the present invention, with the lapse of time after the surgical operation, a collagen fiber tissue intrudes into fine pores of the artificial living body material of the present invention to reinforce the strength thereof, and therefore, it is expected that the function of the artificial joint capsule will be permanently maintained. In this case, by adjusting the pore size, the stretchability or shrinkability of the inclusion membrane and the thickness of the membrane such as a fabric or by coating or soaking a substance positively inducing fibroblasts, the artificial living body material can be fixed more stably and an excellent permanent artificial joint can be obtained. According to one embodiment of the present invention, an artificial joint capsule is formed by using a polyester fiber fabric and this artificial joint capsule can be practically applied to the living body when an excising operation is carried out for remedy of a tumor (mainly a malignant tumor) or an inflammatory disease, and the supporting tissue around the joint is removed. Moreover, by using an artificial joint [formed of a stainless steel, a titanium alloy, other metal, a ceramic or a high-density polyethylene (HDP)] and a living body material (hydroxapatite, stainless steel, a titanium alloy, a titanium alloy, other metal or HDP) in combination, dislocation or deviation can be prevented and the stability and supporting property of the joint can be improved.

According to the present invention, individual joint motions (sliding, stopping and the like) are not substantially hindered, no pain is felt, and a good aesthetic appearance can be realized after the operation.

In the artificial living body composite material of the present invention, since the porous PTFE sheet, the polyester fiber fabric or the like wraps and encloses the artificial bone portion, a stable supporting effect for the artificial bone portion is obtained, and since the separated ligament, muscle or tendon around the joint can be anchored to the artificial living body material of the present invention, the stability, supporting property, and mobility of the joint can be highly improved.

Furthermore, if the artificial bone portion is broken, the scattering of broken pieces can be prevented. Still further, the artificial living body material (joint capsule) of the present invention exerts functions similar to the functions of the joint capsule, that is, reduction of the frictional force by secretion of a functional lubricant fluid and catabolism of wastes in the joint cavity.

More specifically, by intrusion of fibroblasts or cells not eating histiocytes or leucocytes, secretion of the bone fluid and storage of the synovial fluid can be accomplished, and scattering of wastes and worn pieces of the artificial body portion, which is undesirable for the living body, can be prevented.

Furthermore, if the inclusion membrane of a polyester fiber fabric or porous PTFE sheet is coated or impregnated with a bone morphogenetic protein (BMP), induction of a bone is positively promoted and the stability or supporting property of the artificial bone portion formed of a metal or ceramic can be increased. If a filler composed of a metal or ceramic and the inclusion membrane composed of a polyester fiber fabric are used in combination to fill a bone-deficient part or vacant part and the inclusion membrane is anchored to a neighbouring supporting tissue (periosteum, ligament, fascia or muscle tendon), the stability and supporting property of the artificial living body material can be increased. As is apparent from the foregoing description, it is expected that the material can be used for various applications.

(EXAMPLES)

The present invention will now be described in detail with reference to the following examples.

EXAMPLE 1

A. Preparation of Artificial Bone

In a calcium hydroxide solution having a concentration of 0.5 mole/l was gradually dropped a phosphoric acid solution having a concentration of 0.3 mole/l, and the liquid mixture was reacted with stirring until the pH value was 7.5. Hydroxyapatite in which the molar ratio of calcium to phosphorus was 1.66 was obtained, and the product was recovered by filtration and dried to obtain powdery hydroxyapatite. Then, 100 g of the powdery hydroxyapatite was mixed with 35 g of polymethyl methacrylate resin particles of a truly spherical shape having a diameter of 50 to 350 μm and 5 g of cellulose fibers (having a diameter of 5 to 10 μm and a length of 0.5 mm) and the mixture was stirred together with ethanol. The ethanol was then removed by filtration, and 7 to 10 g of the mixture was sealed in a rubber balloon-like tube having a length of 15 cm and a diameter of 2 cm, and the mixture molded under a pressure of 1500 kg/cm² by a hydrostatic pressure press (CIP).

The obtained molded body was dried at room temperature for one whole day and night and placed in an electric furnace, and the molded body was heated to 400° C. at a temperature-elevating rate of 2° C./min to remove the polymethyl methacrylate particles and cellulose fiber by thermal decomposition. Then, the temperature was elevated to 1150° C. and the molded body was sintered at this temperature for 5 hours. The obtained porous calcium phosphate sintered body had a porosity of 40%, in which pores having a diameter of 40 to 210 μm were uniformly distributed and communicated with one another through capillary void paths having a diameter of 4 to 9 μm.

The so-obtained porous molded body was formed into an artificial bone portion as shown in FIGS. 1A and 1B by using a cutter, a lathe and a drill. The outer diameter of the core 1a of the artificial bone portion was 10 mm, the diameter of the hollow portion 1c and 3 mm, and the outer diameter of the hollow projection was 5 mm.

B. Formation of Composite Material

A composite material was obtained by winding a porous polytetrafluoroethylene sheet having a thickness of 1 mm and a width of 3 cm (pore diameter of 0.05 to 5 μm; marketed under the tradename of "Goretex") around the core 1a of the artificial bone portion 1a as shown in FIGS. 1A and 1B.

C. Animal Test

A part having a length of 8 mm was cut from the trunk of a thighbone of a dog and the above-mentioned composite material was inserted into the cut-out part. A first, the upper and lower hollow projection 1a of the composite material was inserted into the marrow cavities on both cut sides of the living body bone (diaphysis) and the artificial bone portion was arranged between both cut sides of the living body bone. The part extending upward and downward from the core 1a of the inclusion membrane was arranged to surround the peripheries of both cut sides of the living body bone and the inclusion membrane was secured to the peripheral faces of the cut sides of the living body bone by using a silk thread. Furthermore, the inclusion membrane was tightly sutured to the neighbouring muscle to fix the artificial bone portion in the immobile state.

Observation was continued over 26 weeks after the operation, and no inflammatory reaction was found with the naked eye at the operated region. Then, the treated thighbone was taken out and observed, and it was found that the peripheral portion of the inclusion membrane was covered with an outer periosteum-forming tissue. When a slice sample of this portion was histologically observed by an optical microscope, it was found that a reborn bone had formed in the interface between the living body bone and the artificial bone portion and osteon had formed in the reborn bone. This reborn bone was integrally bonded to the artificial bone portion and the inclusion membrane was covered with the outer perioteum.

EXAMPLE 2

The procedures of Example 1 were repeated in the same manner except that the sintered calcium phosphate molded body was formed into an artificial living body material for the sternum, which had two fitting projections and the artificial bone portion of this artificial sternum was wrapped with a porous PTFE sheet (Goretex) to form a composite material and shown in FIG. 3.

A solitary myeloid tumor of the sternum of the living body was excised and the above-mentioned composite material was inserted into the excised part, and as shown in FIG. 3, the projection 6 formed in the artificial bone portion 4 was fitted in the collarbone. Furthermore, a steel wire was passed through a wire hole 7 and the artificial bone portion was clamped and fixed to the sternum, first rib, and second rib. Simultaneously, the inclusion membrane was sutured to the surrounding rib ligament, sternomastoid muscle sternum portion, sternothyroid muscle, and sternohyoid muscle by using silk threads.

After the operation, the artificial bone portion sufficiently followed a complicated motion of the sternum joint, and the artificial bone portion was stably fixed without dislocation. Inflamation was not caused and no pain was felt, and bad aesthetic defects did not appear.

EXAMPLE 3

A composite material having a structure as shown in FIGS. 1A and 1B was prepared by using an artificial bone portion formed of metallic titanium and an inclusion membrane composed of a polyester (polyethylene terephthalate) fiber woven fabric. This composite material was used for an operation of replacement of a thighbone.

In this case, a distal osteosarcoma of a right thighbone of the living body was removed by massive excision, and the knee joint was fixed by an intramarrow nail and a bone cement to effect re-construction of the thighbone. When three years had passed after the operation, a leg difference of about 7 cm was caused by the growth and bending of the nail in the marrow and deformation of the bone occurred. The thighbone-elongation operation and extraction of the intramarrow nail and bone cement were performed, and the above-mentioned composite material was inserted.

The inclusion membrane was sutured and fixed to the bone-out portion of the living body and the surrounding muscle, tendon and other soft tissue. The progress was good after the operation and dislocation was not caused in the knee joint. Furthermore, the joint could be bent by about 40°, inflammation was not caused and no pain was felt. The stability was very good.

EXAMPLE 4

An artificial living body composite material comprising an artificial knee joint formed of a ceramic and high-density polyethylene and an inclusion membrane of a polyester fiber fabric covering the artificial bone portion was prepared.

After excision of an osterosarcoma on the near end of the right shinbone, the composite material was used for the replacement of the right knee joint. The composite material was inserted into the excised part and the artificial joint was fixed to the shinbone and thighbone. The inclusion membrane was sutured and anchored to the kneepan ligament, other accessory ligaments, fermoralis muscles and tendons.

The progress was good after the operation, and the artificial joint was fixed stably without dislocation. Inflammation was not caused and no pain was felt.

EXAMPLE 5

The artificial living body composite material 4' shown in FIG. 4 was produced in the following manner.

A coating layer (having a thickness of about 200 μm) was formed by plasma spray coating the same hydroxyapatite particles (having a particle size of 88 μm or less) as those described in Example 1 onto a surface of a non-porous base member produced in a predetermined shape and dimensions from sintered polycrystalline alumina material. Then, the resultant artificial bone portion 42 was wrapped by an inclusion membrane 43 consisting of a porous PTFE sheet (having a thickness of about 1 mm and a pore size of 0.05 to 5 μm).

The artificial bone portion 42 was composed of a principal body 44 and a projection 45 extending from an end of the principal body 44. The principal body 44 had a hollow having a diameter of 3 mm and the outside diameter of a center portion of the principal body 44 was 10 mm. Also, the outside diameter of the projection was 5 mm.

Figure 4:
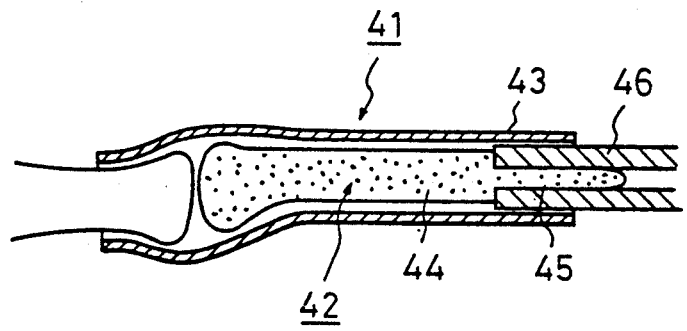
FIG. 4 is a diagram showing a further embodiment of the artificial living body composite material of the present invention.

This artificial living body composite material was subjected to a substitution operation of an animal thighbone in the same manner as that described in Example 1 and shown in FIG. 4. That is, a part of the thighbone 46 was cut, the artificial bone portion 42 of the artificial living body composite material 4 was inserted into the cut-out part, so that the projection 45 was inserted into the remaining portion of the thighbone, and then the inclusion membrane 43 was sutured to the muscle neighbouring the cut-out part and to the kneepan ligament and accessory ligaments.

The progress was good after the operation, and the artificial joint was fixed stably without dislocation. Inflammation was not caused and no pain was felt.

EXAMPLE 6

The same procedures as those mentioned in Example 2 were carried out, except that the artificial bone portion used in this example was composed of a base member consisting of sintered alumina and a coating layer (having a thickness of about 200 μm) formed from hydroxyapatite by a prasma spray coating method.

The progress was good after the operation. The affinity of the artificial bone portion to the living body was good, and thus, the growth of a new bone was good, and the same effects as those described in Example 2 were recognized.

EXAMPLE 7

The same procedures as those described in Example 3 were carried out, except that the artificial bone portion used in this example was composed of a base member made by titanium metal and a coating layer (having a thickness of about 200 μm) formed from hydroxyapatite by the plasma spray coating method.

The same effects as those mentioned in Example 3 were obtained.

EXAMPLE 8

The same procedures as those described in Example 4 were carried out, except that the artificial bone portion used in this example was composed of a base member consisting of a high density polyethylene resin and an alumina coating layer formed on the base member.

The same effects as those described in Example 4 were obtained.

INDUSTRIAL UTILIZABILITY

The present invention provides an artificial living body composite material which can be industrially produced.

In this artificial living body composite material, by combining a specific artificial bone portion with an inclusion membrane wrapped therearound, the fixation stability of the substituted or filled artificial bone portion is enhanced, and a substitution or filling operation for joint portions, which does not cause a dislocation or deviation thereof, becomes possible.

We claim:

1. Artificial living body composite material comprising:
   (a) an artificial bone portion having a predetermined shape and size and consisting essentially of a sintered ceramic material selected from the group consisting of alumina, zirconia and calcium phosphate, said bone potion having a number of spherical independent pores having a size of 1 to 600 μm and communicated with one another and with an exterior space through a number of capillary void paths having a void diameter of 1 to 30 μm; and
   (b) an inclusion membrane which covers said artificial bone portion, said inclusion membrane being in the form of a member selected from the group consisting of sheets, tubes and bags, and at least the main component of said membrane being at least one member selected from the group consisting of woven fabrics, knitted fabrics, felts, nets and nonwoven fabrics comprising a synthetic polymeric material selected from the group consisting of polyester resins and fluorine-containing organic polymer resins.

2. The composite material according to claim 1, wherein said polyester resin is a polyethylene terephthalate resin.

3. The composite material according to claim 1, wherein said fluorine-containing organic polymer resin is a polytetrafluoroethylene resin.

4. The composite material according to claim 1, wherein said porous inclusion membrane consists essentially of a porous polytetrafluoroethylene film.

5. The composite material according to claim 1, wherein said artificial bone portion comprises a base member and a coating layer formed on a surface of the base member.

6. The composite material according to claim 5, wherein said coating layer is porous.

7. The composite material according to claim 5 or 6, wherein said coating layer comprises at least one sintered ceramic material selected from the group consisting of alumina, zirconia, and calcium phosphate.

* * * * *

UNITED STATES PATENT AND TRADEMARK OFFICE
CERTIFICATE OF CORRECTION

PATENT NO. : 5,211,661
DATED : May 18, 1993
INVENTOR(S) : Shinjou et al

It is certified that error appears in the above-indentified patent and that said Letters Patent is hereby corrected as shown below:

On the title page, Item [30]: "May 16, 1986" should read --May 15, 1986--

Signed and Sealed this

Thirty-first Day of May, 1994

Attest:

Attesting Officer

BRUCE LEHMAN
Commissioner of Patents and Trademarks